United States Patent
Boday et al.

(10) Patent No.: US 10,485,875 B2
(45) Date of Patent: Nov. 26, 2019

(54) NANOPARTICLES FUNCTIONALIZED WITH SULFUR-CONTAINING POLYMERS

(71) Applicant: International Business Machines Corporation, Armonk, NY (US)

(72) Inventors: Dylan J. Boday, Tucson, AZ (US); Jeannette M. Garcia, San Leandro, CA (US); James L. Hedrick, Pleasanton, CA (US); Rudy J. Wojtecki, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/914,694

(22) Filed: Mar. 7, 2018

(65) Prior Publication Data
US 2018/0185500 A1 Jul. 5, 2018

Related U.S. Application Data

(62) Division of application No. 14/844,561, filed on Sep. 3, 2015, now Pat. No. 9,950,079.

(51) Int. Cl.
*A61K 47/48* (2006.01)
*A61K 47/20* (2006.01)
(Continued)

(52) U.S. Cl.
CPC ............ *A61K 47/59* (2017.08); *A61K 47/20* (2013.01); *A61K 47/56* (2017.08);
(Continued)

(58) Field of Classification Search
None
See application file for complete search history.

(56) References Cited

U.S. PATENT DOCUMENTS

| 7,824,619 B1 | 11/2010 | Aviram |
| 8,304,257 B2 | 11/2012 | Ackerson et al. |

(Continued)

FOREIGN PATENT DOCUMENTS

| CA | 2779099 A1 | 5/2011 |
| CN | 101929978 A | 12/2010 |

(Continued)

OTHER PUBLICATIONS

Tonga, G.Y., Moyano, D.F., Kim, C.S., Rotellow, V.M.. Current Opinion in Colloid & Interface Science (2014), 19, 49-55.

(Continued)

*Primary Examiner* — Kevin S Orwig
(74) *Attorney, Agent, or Firm* — Patterson + Sheridan, LLP (57) ABSTRACT

A functionalized nanomaterial, such as a nanoparticle, can include a polythioaminal functionalized surface. The polythioaminal linked to the surface of the nanomaterial can be bonded to a compound such as therapeutic and/or diagnostic materials. The thiol-based linkages can be used to bond the polythioaminal to both the nanomaterial and the therapeutic and/or diagnostic materials. Polythioaminals can be prepared via reactions of triazine and dithiols. Polythioaminals thus prepared can be further modified to provide linkages to the nanomaterial and other compounds such as medicinal compound, peptides, and dyes. Nanomaterials including such compounds linked thereto via the polythioaminal can be supplied for therapeutic and/or diagnostic purposes to biological target regions.

20 Claims, 5 Drawing Sheets

Specification includes a Sequence Listing.

(51) Int. Cl.

| | | |
|---|---|---|
| *A61K 47/30* | (2006.01) | |
| *A61K 47/59* | (2017.01) | |
| *A61K 49/00* | (2006.01) | |
| *C08G 73/02* | (2006.01) | |
| *A61K 47/69* | (2017.01) | |
| *A61K 47/56* | (2017.01) | |

(52) U.S. Cl.
CPC ...... *A61K 47/6923* (2017.08); *A61K 47/6929* (2017.08); *A61K 49/0002* (2013.01); *A61K 49/0017* (2013.01); *A61K 49/0065* (2013.01); *C08G 73/0253* (2013.01)

(56) References Cited

U.S. PATENT DOCUMENTS

| | | |
|---|---|---|
| 2005/0013935 A1 | 1/2005 | Iijima et al. |
| 2009/0039018 A1 | 2/2009 | Jordi et al. |
| 2012/0225021 A1 | 9/2012 | Qian et al. |
| 2013/0217037 A1 | 8/2013 | Brisson et al. |
| 2017/0065722 A1 | 3/2017 | Boday et al. |

FOREIGN PATENT DOCUMENTS

| | | |
|---|---|---|
| CN | 103364392 A | 10/2013 |
| EP | 2384439 A1 | 11/2011 |
| WO | 2010087912 A1 | 8/2010 |

OTHER PUBLICATIONS

Giljohann, D.A., Seferos, D.S., Daniel, W.L., Massich, M.D., Patel, P.C., Mirkin, C.A.. Gold Nanoparticles for Biology and Medicine. Angew. Chem. Int. Ed. Engl. (2010), 49(19), 3280-3294.

SEQUENCE LISTING

<160> NUMBER OF SEQ ID NOS: 1

<210> SEQ ID NO 1
<211> LENGTH: 10

```
<212> TYPE: PRT
<213> ORGANISM: Artificial Sequence
<220> FEATURE:
<223> OTHER INFORMATION: Synthesized

<400> SEQUENCE: 1

Cys Leu Leu Lys Lys Leu Leu Lys Lys Cys
1               5                   10
```

NANOPARTICLES FUNCTIONALIZED WITH SULFUR-CONTAINING POLYMERS

CROSS-REFERENCE TO RELATED APPLICATIONS

This application is a divisional of co-pending U.S. patent application Ser. No. 14/844,561, filed Sep. 3, 2015. The aforementioned related patent application is herein incorporated by reference in its entirety.

SEQUENCE LISTING

This application contains a sequence listing submitted electronically via EFS-web, which serves as both the paper copy and the computer readable form (CRF) and consists of a file entitled ROC920150146_Sequence_Listing_ST25.txt, created on Mar. 22, 2018, having a file and byte size of 4 KB, which is incorporated by reference in its entirety.

BACKGROUND

The present disclosure relates to functionalized nanomaterials, and more specifically, to nanoparticles functionalized with polythioaminals.

SUMMARY

According to one embodiment of the present disclosure, a material includes a nanomaterial and a polythioaminal having a structure:

wherein each $R^1$ is independently an organic or heteroorganic species, each $R^2$ is independently a substituent having a molecular weight no more than about 120 Daltons, X is a sulfur bonded species, Z is a linkage to the nanomaterial, and n is an integer greater than or equal to 1. In some examples, X comprises a theranostic compound such as a dye molecule, a biologically active species, or a therapeutic agent, such as a medicinal compound or the like. The nanomaterial can be a nanoparticle. In some embodiments, at least one instance of $R^1$ can include a polyethylene glycol. In general, Z can be anything which links the polythioaminal to the surface of the nanomaterial, inclusive of a direct covalent bond to the surface. Z may include at least one carbon atom. In some examples, $R^2$ is a methyl group.

According to another embodiment of the present disclosure, a method comprises functionalizing a nanomaterial to provide a thiol end group connected thereto. The functionalized nanomaterial is then exposed to a polythioaminal such that the polythioaminal becomes linked to nanomaterial via the thiol end group. The polythioaminal exposed to the functionalized nanomaterial has a general structure:

wherein each $R^1$ is independently an organic or heteroorganic species, each $R^2$ is independently a substituent having a molecular weight no more than about 120 Daltons, and n is an integer greater than or equal to 1. In some embodiments, the method can further comprise exposing the nanomaterial that has the polythioaminal linked thereto to a thiol compound have a general structure HS—X, wherein X is a species including at least one carbon. Species X in some examples can include at least one of an alkyl group, an aromatic group, a peptide, or a nucleotide. Species can X includes a theranostic compound, which in this context refers to compound that has at least one of therapeutic or diagnostic effect. In some embodiments, the nanomaterial can be functionalized by exposing the nanomaterial to a dithiol.

In still another embodiment, a method comprises supplying a nanomaterial to a target region of a biological sample. The nanomaterial has a theranostic compound linked thereto via a polythioaminal having a structure:

wherein each $R^1$ is independently an organic or heteroorganic species, each $R^2$ is independently a substituent having a molecular weight no more than about 120 Daltons, X is the theranostic compound or a linkage thereto, Z is a linkage to the nanomaterial, and n is an integer greater than or equal to 1. In some embodiments, the nanomaterial is a gold nanoparticle.

DETAILED DESCRIPTION

Figure 1:
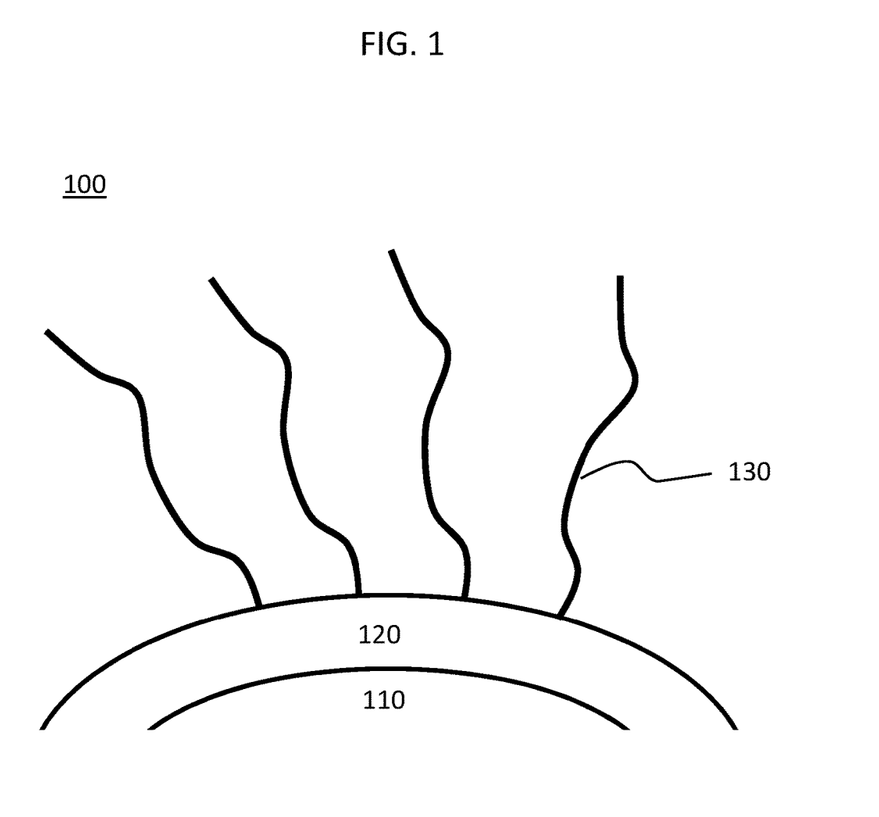
FIG. 1 depicts a nanomaterial functionalized with polythioaminal.

FIG. 1 depicts a nanomaterial 110 functionalized with a polythioaminal. Nanomaterial 110 is, for example, a metal material such as gold. Nanomaterial 110 is, for example, a nanoparticle. Nanomaterial 110 has a surface coating 120. A polythioaminal 130 is covalently bonded to surface coating 120. Surface coating 120 is formed, for example, by contacting nanomaterial 110 with a dilute solution of a dithiol. A dithiol has the general structure (1):

HS—R'—SH     (1)

wherein $R^1$ includes at least one carbon. R' can be an alkyl group, for example, having 1 to 12 carbon atoms ($C_1$ to $C_{12}$), such as a hexyl radical. Surface coating 120 can be formed using, for example, alkane dithiols such as butane dithiol, pentane dithiol, and hexane dithiol, any of which may be used as precursors. Aromatic dithiols such as benzene dithiol, toluene dithiol, and xylene dithiol may also be used as precursors to surface coating 120. The dithiol used in forming surface coating 120 may itself be a polymer species, such as a dithiol-capped polyolefin. Dithio-polyol species, such as dithio-alkane diols, triols, and the like, may also be used in forming surface coating 120.

As noted, nanomaterial 110 can be a nanoparticle. Nanoparticles have been generated with a variety of properties and compositions. Nanoparticles can be composed of materials such as metals, semiconductors, and dielectrics. For example, silicon, cadmium, lead, gadolinium, and gold can be formed into nanoparticles of various dimensions. Gold is particularly useful in many instances because it is generally non-toxic in biological applications.

The outer surface of nanoparticles can be covered with various coatings that serve to minimize interactions between the nanoparticle and its surroundings or otherwise alter properties of the nanoparticle. For example, polymers with at least one thiol end group can be bound to a gold surface. Coatings on nanoparticles can also be utilized to provide for the attachment and delivery of therapeutic or diagnostic agents. For example, medicinal compounds and dyes can be attached to the coated nanoparticle by various means. In some instances, supramolecular complexes can be used to provide a route for the attachment and subsequent delivery or release of therapeutic and diagnostic compounds. That is, for example, a medicinal compound or a dye compound can be linked to coated nanoparticles by supramolecular attachments (electrostatic forces, hydrogen bonding, or intermolecular forces) which may later be weakened or counteracted by changes in environmental conditions of the nanoparticle (changes in solvent conditions, pH variations, temperature increases, etc.). Reliance on supramolecular attachments in this context risks such things as premature or unintended release of the medicinal or dye compounds outside of the intended target area because the attachment is relatively weak and thus potentially responsive to small changes in environmental conditions. Furthermore, supramolecular attachments are subject to stochastic variations in attachment strength, thus continuous random fluctuations between molecules may result in unintended release. Furthermore, the available release/trigger mechanisms for these compounds may be difficult or impossible to tailor as required for many intended applications.

In some instances, it may be preferred to covalently bond the therapeutic and/or diagnostic compounds to the coated nanoparticle. However, compounds that have been covalently bound to nanoparticles may later be difficult detach from the coated nanoparticle because detachment requires breaking of a covalent bond. Simple changes in local solvent conditions, pH changes, or small increases in temperature will generally be insufficient to break a covalent bond. Additionally, making the initial covalent attachment may require many synthetic and purifications steps and/or significant structural modification of the compound being attached. Thus, the provision of therapeutic and/or diagnostic compounds which are covalently attached to a nanoparticle yet have reliable release/trigger mechanisms with respect to changes in environmental conditions is desirable.

Therapeutic compounds can be, for example, medicinal compounds or bioactive materials intended to treat or ameliorate diseases, medical conditions, or the like. Diagnostic compounds can be, for example, fluorescent dyes, imaging markers, or the like. Collectively, therapeutic compounds and diagnostic compounds may be referred to as "theranostic agents" or "theranostic compounds." In an example, a dye molecule and a medicinal compound could be loaded onto a coated nanoparticle such that both the dye and the medicinal compound release from the nanoparticle in response to the same stimulus. The dye could be used to visualize and/or image the release point and the medicinal compound could treat diseased cells proximate to the release point. In another example, the dye and the medicinal compound could be loaded onto the coated nanoparticle such that the dye and the medicinal compound release in response to different stimuli.

Figure 2:
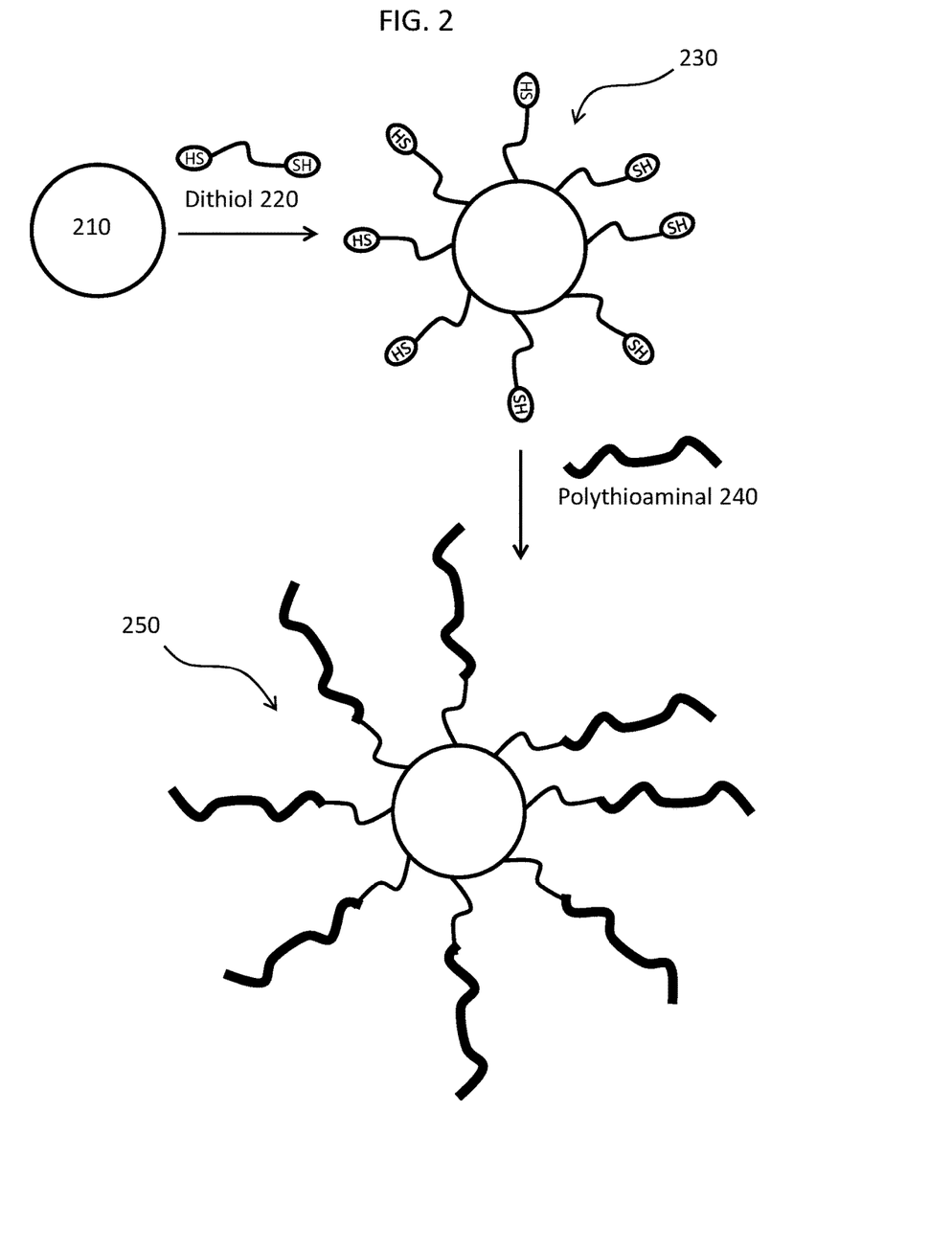
FIG. 2 depicts a process for functionalizing a nanoparticle with polythioaminal.

In FIG. 1, surface coating 120 is depicted as a continuous film or layer, however this is for purposes of explanation, and surface coating 120 may consist of discrete molecules (see e.g., FIG. 2). Furthermore, it is not required that surface coating 120 cover the entire surface of nanomaterial 110 and in various embodiments it would be sufficient for surface coating 120 to cover only some portion of nanomaterial 110. In general, formation of surface coating 120 is intended to promote the later linkage of polythioaminal 130 to the nanomaterial 110. As such, any coating or material which allows polythioaminal 130 to be bonded/linked to nanomaterial 110 can be used for surface coating 120. In some examples, it may be unnecessary to separately provide surface coating 120 and polythioaminal 130 can be modified or designed to include an end group which bonds directly to the surface of nanomaterial 110 in a desired manner. A polythioaminal thus designed or modified can form an equivalent to the surface coating 120 in the functionalized nanomaterial without requiring a separate step of preparing the surface of nanomaterial 110.

A process for preparing a polythioaminal functionalized nanoparticle is depicted in FIG. 2. A nanoparticle 210 corresponds to nanomaterial 110 in this instance. The composition of nanoparticle 210 is not a particular limitation, but here, as an example, nanoparticle 210 comprises gold. Other metals can be used in nanoparticle 210 such as, without limitation: gadolinium (Gd), cadmium (Cd), and lead (Pb). Thus, in some embodiments, nanoparticle 210 can be a gold nanoparticle, a gadolinium nanoparticle, a cadmium nanoparticle, or a lead nanoparticle. In some applications, gold may be preferred as a generally bio-inactive material. In some applications, gadolinium may be useful material for various imaging processes.

In an initial process, nanoparticle 210 is exposed to dithiol 220. A gold surface of nanoparticle 210 reacts with one of the thiol end groups to form a linkage between nanoparticle 210 and the remaining portion of the dithiol 220 molecule. Generally, steric hindrance will prevent both thiol end groups of a single dithiol 220 molecule from attaching to one nanoparticle 210. Similarly, in this context, it may be useful for dithiol 220 to be a relatively low molecular weight compound such as butane dithiol, pentane dithiol, and hexane dithiol. Dilute reactant conditions are also typically used to prevent or at least limit agglomeration of nanoparticles and/or chemical linkage between nanoparticles.

Linkage of dithiol 220 to nanoparticle 210 produces surface coated nanoparticle 230. The attached dithiol 220 molecules on surface coated nanoparticle 230 collectively correspond in this instance to surface coating 120 on nanomaterial 110, which may be discontinuous as described above. Dithiol 220 has the general structure (1) described above.

As depicted in FIG. 2, after surface coated nanoparticle 230 is formed, it is exposed to polythioaminal 240. The polythioaminal 240 has the general structure (2):

(2)

In this general structure (2), each instance of $R^1$ is independently an organic or hetero-organic group. In some cases, each instance of $R^1$ may be the same species. Each instance of $R^2$ is independently an organic or hetero-organic group that may have a molecular weight of not more than about 120 Daltons, and each instance of $R^2$ may be the same species. In each instance, $R^1$ may be a hydrocarbon species, an aromatic and/or aliphatic; a polymer species such as polyethylene glycol, polyol species; or polyether species, any of which may have substituents. In one embodiment, at least one instance of $R^1$ is polyethylene glycol. In another embodiment, each instance of $R^1$ is the same species.

Polythioaminal 240 can be prepared with the following polymerization reaction scheme (3):

(3)

In reaction (3), an N-substituted hexahydrotriazine (HT) is reacted with a dithiol, or a mixture of dithiols, to form a polythioaminal 240, with $R^1$ and $R^2$ as described above. In general, a low molecular weight substituent (e.g., MW≤120 Daltons) is used for $R^2$ to provide higher molecular weight ($M_w$) polymers. However, $R^2$ could be a higher molecular weight substituent (e.g., MW>120 Daltons), but this would typically result in lower molecular weight ($M_w$) polymers. The reaction may be performed in a solvent medium such as N-methyl pyrrolidone (NMP), or other suitable solvent, to control viscosity. Each instance of $R^2$ may be any group resulting in a byproduct ($R^2$—$NH_2$) in the reaction scheme (3) which is volatile at a temperature below about 200° C., under vacuum if necessary. In general, if the generated byproduct incorporating the $R^2$ group can be removed from the reaction mixture, polymer growth will be enhanced. For example, each instance of $R^2$ may independently be hydrogen, fluorine, methyl, or an alkyl group such as ethyl, propyl, butyl, hexyl, or cyclohexyl.

For the dithiol in reaction (3), alkane dithiols such as butane dithiol, pentane dithiol, and hexane dithiol may be used. Aromatic dithiols such as benzene dithiol, toluene dithiol, and xylene dithiol may also be used. The dithiol may be a polymer species, such as a dithiol-capped polyolefin. Dithio-polyol species may also be used, such as dithio-alkane diols, triols, and the like.

An example reaction for formation of polythioaminal 240 according to reaction scheme (3) is the reaction between 1,3,5-trimethylhexahydrotriazine and 1,6-hexanedithiol, as follows in reaction (4):

(4)

Reaction (4) may be performed using NMP as solvent, or using the reactants alone as solvent. For example, the reaction (4) may be performed in excess triazine up to about 2 equivalents, such as from 1.3 to 1.5 equivalents, for example about 1.3 equivalents. The precursors may be obtained from commercial suppliers or may be synthesized.

Reaction (3) and reaction (4) may be performed according to the following exemplary processing. In a stirred vessel, the dithiol precursor is added to 1.3 equivalents of the HT precursor. The vessel is purged with nitrogen or other inert gas and sealed, and the reaction mixture is heated to 85° C. The reaction mixture is maintained at 85° C. for 18 hours to form oligomers. Vacuum is then applied to the vessel to remove volatile byproducts, driving growth in molecular weight of the resulting polymer molecules according to LeChatelier's Principle. The reaction is allowed to proceed for 24 hours, during which stirring may cease due to viscosity of the mixture. The resulting polymer is typically optically transparent and may range from a solid to a viscous liquid.

A method of forming a polythioaminal includes mixing an N-substituted hexahydrotriazine and a dithiol in a vessel to form a first mixture, and heating the first mixture to form a polythioaminal polymer. The substituent bonded to a nitrogen atom of the N-substituted hexahydrotriazine is incorporated into an amine byproduct during polymerization. The substituent may be selected such that the ultimate byproduct is volatile at temperatures up to about 200° C. so that the byproduct can be removed during polymerization to increase molecular weight of the resultant polymer. The byproduct can be removed by pumping off the generated vapor and/or by inclusion of molecules or materials which remove or otherwise sequester the byproduct from the remaining reactants. The method may further comprise adding a thiol-reactive material to the polythioaminal polymer to form a second mixture, and the second mixture may be heated to form an end-modified polythioaminal polymer, which may be, or include, a theranostic agent. A solvent may be added to the N-substituted hexahydrotriazine or the dithiol prior to forming the first mixture, may be added during forming the first mixture, may be added to the first mixture after forming the first mixture, or may be added to the second mixture after forming the second mixture. The end-modified polythioaminal polymer may be formed linked to a nanoparticle or nanomaterial or may be subsequently attached to a nanoparticle or nanomaterial.

A higher reaction temperature for the formation of a polythioaminal may be used in some cases to promote removal of byproducts during the reaction. One or more of the substituents bound to the nitrogen atoms of the hexahydrotriazine precursor will form a byproduct during the polymerization reaction, so the substituent is generally chosen such that a byproduct incorporating a $R^2$ group from the N-substituted hexahydrotriazine is volatile at temperatures below 200° C. This byproduct will typically be a bis-amine that breaks down further to an amine. The byproduct may volatilize from heating alone, or vacuum may be applied to encourage volatility. For at least this reason, higher temperatures may promote development of higher molecular weight in the polymer through removal of byproducts. Alternatively, the byproducts can be removed or otherwise sequestered from remaining reactants by inclusion of a "scavenger" type molecule that reacts with (or otherwise removes) the byproducts.

Formation of the polythioaminal polymer may be controlled by adjusting temperature of the reaction mixture and solvent content. Solvents such as N-methyl-2-pyrrollidone or other suitable aprotic solvents, which may include dimethylsulfoxide (DMSO), N,N-dimethylformamide (DMF), N,N-dimethylacetamide (DMA), propylene carbonate (PC), and propylene glycol methyl ether acetate (PGMEA), of which any mixture may also be used. Application of heat and vacuum increases the resultant polythioaminal molecular weight (weight-average or number average) up to a point. Because the polymer itself begins to decompose at temperatures above about 200° C., additional heating beyond this level may be counter-productive. In one aspect, polymerization is enhanced using hexahydrotriazine N-substituents ($R^2$) having a molecular weight less than about 120 Daltons. In another aspect, polymerization is enhanced using hexahydrotriazine N-substituents ($R^2$) which provide byproducts having a room temperature vapor pressure of at least 10 Torr. Polythioaminals formed according to scheme (3) may, in some embodiments, have a weight-average molecular weight ($M_w$) from 3,800 Daltons to 36,000 Daltons or at least a weight-average molecular weight ($M_w$) of 10,000 Daltons.

As depicted in reaction (3) and reaction (4), the dithiol is a single type of compound, but it is also possible to use a mixture of dithiols in these reactions. A plurality of different dithiol precursors may be used to make a copolymer, terpolymer, or higher degree of mixed polymer. The polythiolaminal 240 may thus be a mixed polymer, such as a copolymer having the general formula (5):

(5)

where each instance of $R^3$ is independently an organic or hetero-organic group different from $R^1$, and each instance of $R^3$ may be the same species. As above in structure (2), each instance of $R^1$ is independently an organic or hetero-organic group, each instance of $R^1$ may be the same species, each instance of $R^2$ is independently an organic or hetero-organic group that may have a molecular weight of not more than about 120 Daltons, each instance of $R^2$ may be the same species, and m and n are each integers greater than or equal to 1. By sequencing and controlling availability of different dithiol precursors, mixed polymer (5) may be a prepared as a block copolymer.

It should also be noted that more than one HT precursor may be used to make a polymer according to reaction (3). A random copolymer may be made by simultaneously using two different triazine precursors with one dithiol precursor. A block copolymer may be made by making a first segment using a first triazine precursor, making a second segment using a second triazine precursor, and then joining the first and second segments using the first triazine precursor, the second triazine precursor, or a mixture of the first and second triazine precursors. And as noted, various mixed polymers may be made by using mixtures of dithiol precursors.

Polythioaminals of structure (2) and structure (5) have thiol end groups. These thiol end groups are reactive, and polythioaminals of structure (2) and structure (5) may be further modified according to the following general scheme (6):

(6)

In general, X and Z may be any thiol reactive species. Of particular use, at least one of X or Z may be a therapeutic agent for treating a medical condition. X and/or Z may be a species selected from the group consisting of hydrogen, an alkane thiol, an aromatic thiol such as a thiophenol or a thioaniline, a peptide, a protein, a thio-acid, a nucleotide, and combinations thereof, with the proviso that X and Z are not both hydrogen. X and/or Z may be a reactive or non-reactive species, a cargo, a linking group, a medicinal compound, a functional species for further modification after initial synthesis of the product polymer of scheme (6), a polymerization starter, a chemical species capable of initiating depolymerization, or a combination of any of the foregoing. Any of the above species may be a linking species (or group) or a non-linking species (or group).

The reaction of HS—X and HS—Z with the polythioaminal of structure (2) or (5) may occur simultaneously or may be performed in sequence with either component being provided first or second. In some instances, polythioaminal compounds with two X (or Z) end groups rather than one of each of X and Z may result. In a particular embodiment, the HS—Z compound can be the surface coated nanoparticle 230 and polythioaminal 240 can have the structure (2) or (5). The reaction between the thiol end groups of surface coated nanoparticle 230 and polythioaminal 240 provides a polythioaminal functionalized nanoparticle 250. While polythioaminal functionalized nanoparticle 250 is depicted having each available end of the attached dithiol 220 molecules linked to a polythioaminal 240, such is not required. Unreacted ends of dithiol may remain depending on amounts of polythioaminal 240 available for reaction, steric effects for already linked polythioaminal 240 molecules, and the like. Likewise the actual number and specific arrangement of available thiol end groups on the depicted nanoparticle in FIG. 2 is not necessarily reflective of the number and arrangement in an actual material. Similarly, the depiction in FIG. 2 regarding relative sizes of the various elements does not necessarily correspond to actual size relations between these elements.

Figure 3:
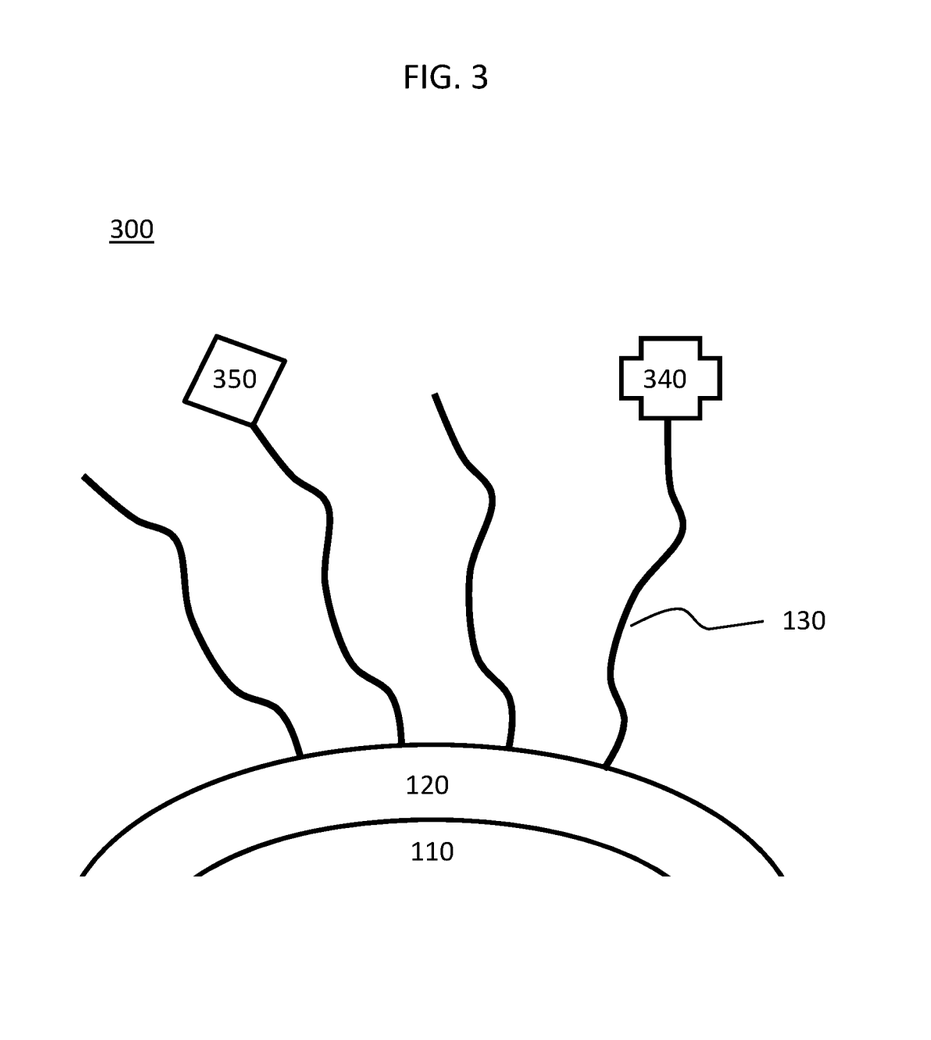
FIG. 3 depicts a polythioaminal-functionalized nanomaterial loaded with a diagnostic and/or therapeutic compound.

With regard to FIG. 3, a nanomaterial is depicted as having theranostic compounds loaded thereon. The theranostic loaded nanomaterial 300 is substantially similar to the polythioaminal functionalized nanomaterial 100 described above, except for the addition of theranostic compounds 340 and 350. Theranostic compounds 340 and 350 are linked to the polythioaminal 130. Theranostic compound 340 is, for example, a medicinal compound or other therapeutic agent intended to treat a medical condition. Theranostic compound 350 is, for example, a fluorescent dye or other marker compound intended to aid diagnosis of a medical condition or the like. Though theranostic loaded nanomaterial 300 is depicted as including both theranostic compounds 340 and 350, it is not required to attach different theranostic compounds to each theranostic loaded nanomaterial 300. That is, the nanomaterial may be loaded with only therapeutic compounds (e.g., 340) or only diagnostic compounds (e.g., 350). Similarly, the number of theranostic compound types is not limited to two and any number of different types of theranostic compounds may be included when synthetically feasible.

Figure 4:
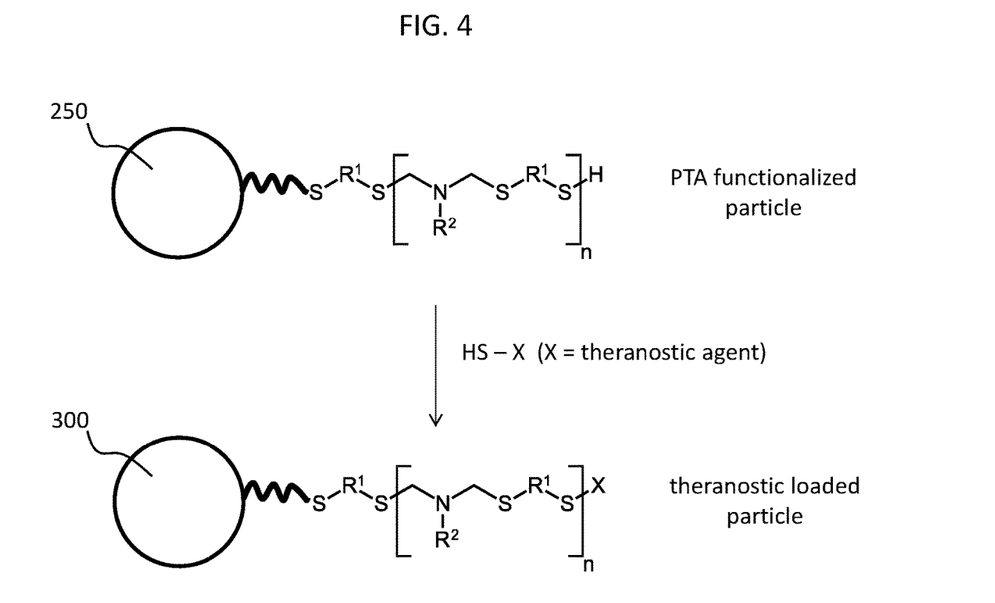
FIG. 4 depicts a process for loading a polythioaminal-functionalized nanoparticle with a diagnostic and/or therapeutic compound.

FIG. 4 depicts a process for preparing a theranostic loaded nanomaterial 300. A polythioaminal functionalized nanoparticle 250 is depicted. A particular polythioaminal portion is depicted in detail. The polythioaminal portion depicted corresponds in general to the polythioaminal 240 used in preparing polythioaminal functionalized nanoparticle 250 according to the process of FIG. 2. Other polythioaminal portions present in the polythioaminal functionalized nanoparticle 250 are not depicted in detail for sake of clarity. The polythioaminal functionalized nanoparticle 250 is exposed to a compound HS—X. Here in this example, X is a theranostic compound. The available thiol end of the polythioaminal portion of nanoparticle 250 reacts with HS—X in a manner similar to scheme (6) such that theranostic compound X is linked to the nanoparticle 250 to thereby provide theranostic loaded nanomaterial 300.

Alternatively, X need not itself be a theranostic compound or otherwise active compound, but rather X can be a linking group such that either upon initial reaction or by subsequent processing, the following structure may result:

(7)

where K is any species bondable to X, and $R^1$, $R^2$, and n are defined as above. Z may be a linkage to a nanoparticle. The linkage to the nanoparticle in some examples may be direct bonding to the surface of the nanoparticle when the nanoparticle has a thiol-reactive surface such as a gold surface.

K may be another polythioaminal segment that links to X via thiol reactivity, such as X is linked to a polythioaminal according to scheme (6), or K may be any other desired species, for example another polymer, peptide, reactive or non-reactive species, cargo, linking group, functional species, polymerization starter, or depolymerization starter that links to X via any suitable linkage. K may also be a species selected from the group consisting of hydrogen, an alkane thiol, an aromatic thiol such as a thiophenol or a thioaniline, a peptide, a protein, a thio-acid, a nucleotide, and combinations thereof.

A nucleotide useable as the sulfur-bonded group X may be a thiol modified oligonucleotide, as in either of the following:

Other species of interest for forming the sulfur-bonded groups X include: dimercaptosuccinic acid tiopronin and the protein known as RANTES or chemokine ligand 5.

Polymer properties may be tuned by selecting the $R^1$ and $R^2$ groups. In particular, interaction of the polymer with water may be tuned by providing various hydrophilic and/or hydrophobic substituents. By using a large hydrophilic dithiol and a small hydrophobic substituted HT, a water-soluble polythioaminal may be made. For example, a polythioaminal 240 prepared according to scheme (3) using a polyethylene glycol dithiol and 1,3,5-trimethylhexahydrotriazine as reactants can be water soluble. Slow degradation of such a polymer into non-toxic components provides the potential for therpeutic delivery agents that do not have substantial toxic effects.

In one example, the thiol-containing amphiphilic alpha-helical peptide CLLKKLLKKC—NH$_2$ (SEQ. ID: NO: 1) was attached to a water-soluble polythioaminal polymer by mixing the peptide and polymer under mild heating. Initially, the peptide was observed to form a white powder phase in the viscous polymer. Maintaining the reaction mixture at 85° C. for 8 hours produced a single phase polymer-peptide product.

A method of forming a material includes mixing an N-substituted hexahydrotriazine and a dithiol in a vessel to form a first mixture, and heating the first mixture to form a polythioaminal polymer. Some of the substituents bonded to nitrogen atoms in the N-substituted hexahydrotriazine are ultimately incorporated into an amine byproduct during the polymerization reaction. These substituents should thus generally be selected such that the byproduct is volatile at temperatures up to about 200° C. so that the generated byproduct can be removed from the polymerization reaction mixture and thereby to increase molecular weight of the final polymer by driving the polymerization reaction forward.

The method may further comprise adding a thiol-reactive material to the polythioaminal polymer to form a second mixture, and the second mixture may be heated to form an end-modified polythioaminal polymer, which may be a therapeutic agent. A solvent may be added to the N-substituted hexahydrotriazine or the dithiol prior to forming the first mixture, may be added during forming the first mixture, may be added to the first mixture after forming the first mixture, or may be added to the second mixture after forming the second mixture. The end-modified polythioaminal polymer may be formed linked to a nanoparticle or nanomaterial or may be subsequently attached to a nanoparticle or nanomaterial.

Figure 5:
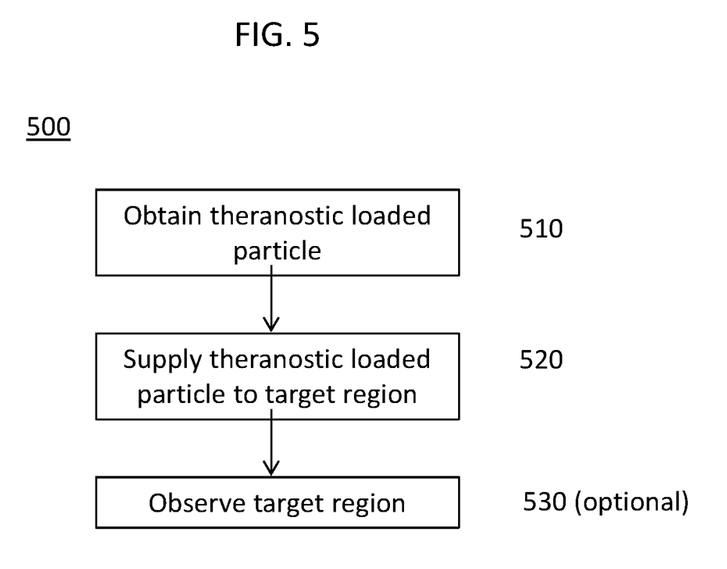
FIG. 5 depicts a process of using a diagnostic and/or therapeutic compound loaded polythioaminal-functionalized nanoparticle.

FIG. 5 depicts a method of using a theranostic loaded particle. In method 500, a theranositc loaded particle is obtained in element 510 of the method. The theranostic loaded particle thus obtained may be, for example, a theranostic loaded nanomaterial 300, which in this instance may be a nanoparticle. The theranostic compounds loaded on the particle may include a dye molecule and/or a therapeutic compound. Theranostic loaded nanoparticle is supplied to a target region in element 520 of the method. The target region can be, for example, a portion of a body, tissue, organs, a living cell, or the like, either in vivo or in an extracted sample. The theranostic loaded particle can be supplied to the target region in a controlled manner such as localized injection or the like or may be supplied in a more generalized manner to a region or body including the target region within. The linkage between the nanoparticle and the theranostic load can be reversible and/or degradeable. For example, the linkage can be water soluble, temperature sensitive, chemically sensitive, pH sensitive, or otherwise altered by environmental stimulus. When the linkage is temperature sensitive, linkage between the theranostic load and the nanoparticle may be broken or reversed by localized heating. Localized heating can be achieved by, for example, exposure of the nanoparticle to microwave or other radiation. In some embodiments, it may be unnecessary for the theranostic load to be detached from the nanoparticle for the therapeutic or diagnostic effect to be achieved. For example, the theranostic load may be bio-active even while attached to the nanoparticle. In element 530 of the method, the target region may be observed. Observation of the target region may include imaging of the target region. Imaging may include detecting a dye included in the theranostic loaded particle or interaction of the nanoparticle and/or theranostic load with electromagnetic radiation.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing is directed to embodiments of the present invention, other and further embodiments of the invention may be devised without departing from the basic scope thereof, and the scope thereof is determined by the claims that follow.

What is claimed is:

1. A material, comprising:
a nanoparticle; and
a polythioaminal having a structure:

wherein:
each $R^1$ is independently a hydrocarbon species, an aromatic species, a polyol species, or a polyether species,
each $R^2$ is independently a hydrogen, a fluorine, an alkyl substituent, a cycloalkyl substituent, or an aromatic substituent, wherein each $R^2$ has a molecular weight no more than 120 Daltons,
X is a hydrogen, an alkane thiol, an aromatic thiol, a peptide, a thio-acid, a nucleotide, and combinations thereof,
Z is a linkage to the nanoparticle, the linkage comprising an alkane thiol, an aromatic thiol, a peptide, a thio-acid, a nucleotide, and combinations thereof, and
n is an integer greater than or equal to 1.

2. The material of claim 1, wherein X includes a dye molecule.

3. The material of claim 1, wherein X includes a fluorescent dye.

4. The material of claim 1, wherein X includes a thiol-modified oligonucleotide, a thiol-containing organic acid, or SEQ. ID NO: 1.

5. The material of claim 1, wherein X is a peptide.

6. The material of claim 1, wherein the nanoparticle is a metal nanoparticle.

7. The material of claim 1, wherein at least one instance of $R^1$ includes a polyethylene glycol.

8. The material of claim 1, wherein Z includes at least one carbon atom.

9. The material of claim 1, wherein at least one instance of $R^1$ is a n-hexyl group.

10. The material of claim 1, wherein
the nanoparticle is a gold nanoparticle,
at least one instance of $R^1$ comprises a polyethylene glycol,
$R^2$ is a methyl group,
Z includes at least one carbon atom, and
X comprises a peptide or a nucleotide.

11. The material of claim 1, wherein
the nanoparticle is a gold nanoparticle,
at least one instance of $R^1$ comprises a polyethylene glycol,
$R^2$ is a methyl group,
Z includes at least one carbon atom, and
X includes at least one of an alkyl group, an aromatic group, a peptide, or a nucleotide.

12. A functionalized nanoparticle, comprising:
a nanoparticle; and
a polythioaminal having a structure:

wherein:
each $R^1$ includes a polyethylene glycol group,
each $R^2$ is a methyl group,
X is a hydrogen, an alkane thiol, an aromatic thiol, a peptide, a thio-acid, a nucleotide, and combinations thereof,
Z includes a thiol linkage to the nanoparticle, the thiol linkage comprising an alkane thiol, an aromatic thiol, a peptide, a thio-acid, a nucleotide, and combinations thereof, and
n is an integer greater than or equal to 1.

13. The functionalized nanoparticle of claim 12, wherein X is a dye molecule.

14. The functionalized nanoparticle of claim 12, wherein X includes at least one of a peptide or a nucleotide.

15. The functionalized nanoparticle of claim 12, wherein X includes at least one of an alkyl group, an aromatic group, a peptide, or a nucleotide.

16. The functionalized nanoparticle of claim 12, wherein the nanoparticle is a metal nanoparticle or a silicon nanoparticle.

17. The material of claim 1, wherein each $R^2$ is independently a hydrogen, a fluorine, a methyl, an ethyl, a propyl, a butyl, a hexyl, or a cyclohexyl group.

18. The material of claim 1, wherein the nanoparticle comprises silicon.

19. The material of claim 6, wherein the metal nanoparticle comprises one or more of gold, gadolinium, cadmium, or lead.

20. The functionalized nanoparticle of claim 16, wherein the metal nanoparticle comprises one or more of gold, gadolinium, cadmium, or lead.

* * * * *